US010221255B2

United States Patent
Marguerre et al.

(10) Patent No.: US 10,221,255 B2
(45) Date of Patent: Mar. 5, 2019

(54) COMPOSITION FOR THE IMMEDIATE STOPPING OF A FREE-RADICAL POLYMERIZATION

(71) Applicant: BASF SE, Ludwigshafen (DE)

(72) Inventors: Ann-Kathrin Marguerre, Mannheim (DE); Christian Raith, Mannheim (DE); Christof Kujat, Neustadt (DE); Friedrich-Georg Martin, Heidelberg (DE); Daher Michael Badine, Mannheim (DE); Karolin Geyer, Ludwigshafen (DE); Ansgar Schaefer, Karlsruhe (DE); Nikolaus Nestle, Heidelberg (DE); Murat Cetinkaya, The Hague (NL); Eduard Schreiner, Mannheim (DE); Reiner Weiler, Freisbach (DE); Peter Zurowski, Landau (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/735,007

(22) PCT Filed: Jun. 15, 2016

(86) PCT No.: PCT/EP2016/063796
§ 371 (c)(1),
(2) Date: Dec. 8, 2017

(87) PCT Pub. No.: WO2016/202883
PCT Pub. Date: Dec. 22, 2016

(65) Prior Publication Data
US 2018/0171035 A1  Jun. 21, 2018

Related U.S. Application Data

(60) Provisional application No. 62/180,625, filed on Jun. 17, 2015.

(30) Foreign Application Priority Data

Jun. 17, 2015 (DE) .................. 10 2015 211 083

(51) Int. Cl.
*C08F 2/42* (2006.01)
*C08F 2/38* (2006.01)
*C07C 51/50* (2006.01)

(52) U.S. Cl.
CPC .............. *C08F 2/42* (2013.01); *C07C 51/50* (2013.01); *C08F 2/38* (2013.01); *Y02P 20/542* (2015.11)

(58) Field of Classification Search
CPC ...... C08F 2/38; C08F 2/40; C08F 2/42; C07C 51/50
See application file for complete search history.

(56) References Cited

U.S. PATENT DOCUMENTS

| | | | |
|---|---|---|---|
| 4,581,249 A | 4/1986 | Solomon et al. | |
| 4,665,185 A | 5/1987 | Winter et al. | |
| 4,670,131 A | 6/1987 | Ferrell | |
| 5,322,912 A | 6/1994 | Georges et al. | |
| 5,322,960 A | 6/1994 | Sakamoto et al. | |
| 5,412,047 A | 5/1995 | Georges et al. | |
| H1957 H | 4/2001 | Fried et al. | |
| 2015/0337056 A1* | 11/2015 | Koch et al. ............... | C08F 2/42 526/83 |

FOREIGN PATENT DOCUMENTS

| | | |
|---|---|---|
| CN | 1052847 A | 7/1991 |
| DE | 1618141 | 10/1970 |
| DE | 19510184 A1 | 9/1996 |
| DE | 19602538 A1 | 7/1997 |
| DE | 19651307 A1 | 6/1998 |
| DE | 10036959 A1 | 2/2002 |
| DE | 10325050 A1 | 12/2004 |
| DE | 102005035103 A1 | 2/2007 |
| DE | 102005055815 A1 | 5/2007 |
| DE | 102007055086 A1 | 5/2009 |
| DE | 102013000128 A1 | 7/2014 |
| EP | 0135280 A2 | 3/1985 |
| EP | 0765856 A1 | 4/1997 |
| EP | 2017293 A1 * | 1/2009 ................ C08F 2/40 |
| EP | 2017293 A1 | 1/2009 |
| JP | 5-320217 A | 12/1993 |
| WO | 99/21893 A2 | 5/1999 |
| WO | 2008/135482 A2 | 11/2008 |

OTHER PUBLICATIONS

Mieszkowski et al, Journal of Liquid Chromatography & Related Technologies, Influence of the Anionic Part of 1-Alkyl-3-Methylimidazolium—Based Ionic Liquids on the Chromatographic Behavior of Perazine in RP-HPTLC, 2015, 38, pp. 1499-1506. (Year: 2015).*

* cited by examiner

*Primary Examiner* — Paul A Zucker
(74) *Attorney, Agent, or Firm* — Oblon, McClelland, Maier & Neustadt, L.L.P.

(57) ABSTRACT

A composition for the immediate stopping of a free-radical polymerization comprises a) an inhibitor for the free-radical polymerization selected from among phenothiazines, b) an aprotic solvent and c) an ionic liquid. It serves to stabilize free-radically polymerizable monomers against free-radical polymerization. For the immediate stopping of free-radical polymerizations, the composition is added to a free-radically polymerizing system.

15 Claims, 6 Drawing Sheets

COMPOSITION FOR THE IMMEDIATE STOPPING OF A FREE-RADICAL POLYMERIZATION

The invention relates to a composition for the immediate stopping of a free-radical polymerization, the use thereof for the stabilization of free-radically polymerizable monomers against free-radical polymerization and a method for the immediate stopping of free-radical polymerizations.

The premature polymerization of acrylic monomers in the form of a runaway reaction can lead to vaporization of monomers because of the large enthalpy of reaction. The associated pressure increase can result in, for example, storage vessels bursting and vapors formed igniting, so that an explosion can occur in such an event. This leads to a hazard to persons, goods and the environment. Acrylic acid is classified as particularly critical from a safety point of view since, owing to the high vinyl monomer density, it has a high specific enthalpy of reaction and with a boiling point of 141° C. readily vaporizes during the runaway reaction. One possible way of stopping the incipient runaway reaction is the addition of inhibitors to the polymerizing system.

The use of inhibitors such as hydroquinone, hydroquinone monomethyl ether, p-benzoquinone, p-nitrosophenol (PNP), phenothiazine (PTZ), 4-hydroxy-2,2,6,6-tetramethyl-1-oxylpiperidine (OH-tempo) or methylene blue for stabilizing acrylic acid and methacrylic acid against undesirable free-radical polymerization is known from the German patent application DE 100 36 959 A1.

Phenothiazines are effective inhibitors of free-radical polymerization. However, phenothiazines have a very low solubility in conventional solvents. However, the use of highly dilute solutions is disadvantageous in the case of an emergency when large amounts of inhibitor have to be introduced in a short time.

EP 2017293 A1 discloses mixtures comprising an inhibitor of free-radical polymerization and an ionic liquid and the use thereof for the stabilization of free-radically polymerizable monomers. Although ionic liquids have a high solvent capability for phenothiazines, the high viscosity of the solutions is disadvantageous for rapid mixing into monomers in an emergency.

WO 99/21893 discloses a method for the immediate stopping of free-radical polymerizations by addition of a phenothiazine-comprising solution whose solvent consists to an extent of at least 50% of its weight of an N-alkylpyrrolidone. It is desirable to have alternative solvents since N-alkylpyrrolidones such as N-methylpyrrolidone (NMP) are classified as being toxicologically problematical.

It is an object of the invention to provide a composition for the rapid stopping of a free-radical polymerization, which composition has a high inhibitor concentration and reasonable viscosity and whose solvent system is inert toward monomers such as acrylic acid.

The object is achieved by a composition which comprises a) a free-radical polymerization inhibitor selected from among phenothiazines, b) an aprotic solvent and c) an ionic liquid.

The invention further provides a method for the immediate stopping of free-radical polymerizations, wherein the abovementioned composition is added to a free-radically polymerizing system.

The composition of the invention preferably does not comprise any inhibitor which remains undissolved over a temperature range from 0 to 40° C. It is (at atmospheric pressure) preferably present as a single phase, i.e. as a homogeneous mixture without phase separation, over a temperature range from 0 to 40° C. However, it can also be present in the form of two-phase liquid systems.

The composition of the invention comprises at least one, in particular precisely one, free-radical polymerization inhibitor which is selected from among phenothiazines.

As is known, free-radical polymerization is a chain reaction in which free radicals are formed in the initiation step and the monomers to be polymerized add onto these radicals until termination by combination or disproportionation of two macroradicals or a reaction thereof with chain transfer substances or impurities such as oxygen occurs (cf. Römpp Online, 2007, "Radikalische Polymerisation").

As is known, inhibitors act as free-radical scavengers and thus inhibit the formation of free radicals in the initiation step of the chain reaction (cf. Römpp Online, 2007, "Inhibierung").

Phenothiazines are effective inhibitors of free-radical polymerization. Suitable phenothiazines are those of the general formula I:

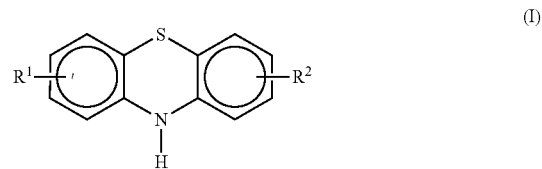

where $R^1$ and $R^2$ are each, independently of one another, hydrogen, $C_6$-$C_{10}$-aryl, $C_7$-$C_{11}$-aralkyl, $C_7$-$C_{16}$-alkaryl or $C_1$-$C_{12}$-alkyl.

Suitable phenothiazines are phenothiazine, 2-methylphenothiazine, 2-octylphenothiazine, 2-nonylphenothiazine, 2,8-dimethylphenothiazine, 3,7-dimethylphenothiazine, 3,7-diethylphenothiazine, 3,7-dibutylphenothiazine, 3,7-dioctylphenothiazine and 2,8-dioctylphenothiazine, 3,7-dinonylphenothiazine, 2,8-dinonylphenothlazine, 2-(α,α-dimethylbenzyl)phenothiazine, 3,7-bis(α,α-dimethylbenzyl)phenothiazine and 2,8-bis(α,α-dimethyibenzyl)phenothiazine.

Preference is given to using phenothiazine ($R^1$=$R^2$=H) as inhibitor in the composition of the invention.

The composition comprises an aprotic solvent or a combination of aprotic solvents. The aprotic solvent does not comprise any acidic hydrogen atoms, i.e. it does not have hydrogen atoms bound to an oxygen atom or nitrogen atom.

The aprotic solvent generally has a boiling point of at least 80° C. at atmospheric pressure, preferably at least 100° C. and in particular at least 150° C.

The aprotic solvent preferably does not comprise any atoms other than carbon, oxygen, nitrogen and/or hydrogen; in particular no atoms other than carbon, oxygen and/or hydrogen.

The aprotic solvent usually has a relative static permittivity $\varepsilon_r$ (also referred to as dielectric constant, dielectric number or permittivity number) as liquid pure substance in the range from 3 to 50, preferably from 4 to 38, particularly preferably from 5 to 20, at a temperature of 293.15 K and a pressure of $1.0133 \cdot 10^5$ Pa (=atmospheric pressure) (the relative static permittivity of free space=1). A suitable source with data on relative static permittivities of suitable relevant aprotic substances is, for example, the HANDBOOK of CHEMISTRY and PHYSICS, 92nd Edition (2010-2011), CRC PRESS. As an alternative or in addition, the aprotic solvent has a position in the Hansen solubility space which is such that $$\sqrt{4(\delta_D-17)^2+(\delta_P-11)^2+(\delta_H-6)^2} \leq 9 \quad \text{(formula 1)}.$$

The value will hereinafter also be referred to as solubility distance $R_a$. The definition and calculation of the solubility parameters in the three-dimensional Hansen solubility space are described in: C. M. Hansen: "The three dimensional solubility parameters" J. Paint Technol. 39, 105 (1967). In this Hansen space, $\delta_D$ denotes the LONDON dispersion forces, $\delta_P$ denotes the Debye interaction forces between permanent dipoles and also the Keesom interaction forces between induced and permanent dipoles and $\delta_H$ denotes the specific interaction forces (hydrogen bonds, acid/base, donor/acceptor, etc.). The unit of the parts of the parameters is in each case [MPa$^{1/2}$].

The Hansen solubility parameters for many solvents are tabulated in standard works such as Hansen Solubility Parameters: A User's Handbook, C. M. Hansen, 2007, 2nd Edition. It is also possible to use known modeling software, for example HSPIP 3.1.14 (3rd Edition), developed and marketed by C. M. Hansen, in order to calculate the Hansen solubility parameters on the basis of the chemical structure of the solvent. The Hansen solubility parameters used here relate to room temperature, about 23° C.

By way of example, the respective parts of the solubility parameters of various solvents ($\delta_D$, $\delta_P$, $\delta_H$) and the solubility distances calculated from formula 1 are shown in the following table.

TABLE 1

Hansen solubility parameters and relative static permittivities $\varepsilon_r$ for various solvents

| Solvent | $\delta_D$ | $\delta_P$ | $\delta_H$ | $R_a$ | $\varepsilon_r$ at 20° C. |
|---|---|---|---|---|---|
| DMSO | 18.4 | 16.4 | 10.2 | 7.4 | 47.3 |
| Sulfolane | 17.8 | 17.4 | 8.7 | 7.1 | 42.7 |
| Benzonitrile | 18.8 | 12.0 | 3.3 | 4.6 | 25.7 |
| Dimethyl succinate | 16.1 | 7.7 | 8.8 | 4.7 | 7.3 |
| Methyl benzoate | 18.9 | 8.2 | 4.7 | 4.9 | 6.7 |
| γ-Butyrolactone | 18.0 | 16.6 | 7.4 | 6.1 | 41.4 |
| Acetonitrile | 15.3 | 18.0 | 6.1 | 7.8 | 36.8 |
| Cyclohexanone | 17.8 | 8.4 | 5.1 | 3.2 | 16.1 |
| Methyl butyl ketone | 15.3 | 6.1 | 4.1 | 6.3 | 14.5 |
| Morpholine | 18.0 | 4.9 | 11.0 | 8.1 | 7.8 |
| Dibutyl adipate (Cetiol B) | 16.4 | 4.3 | 5.9 | 6.8 | 3.0 |
| Di(2-ethylhexyl) adipate (Plastomoll DOA) | 16.2 | 4.6 | 7.7 | 6.8 | 2.1 |
| C$_{10}$-fatty acid dimethylamide (Agnique AMD 10) | 16.6 | 6.7 | 5.7 | 4.4 | 13.8 |
| N-Methylimidazole | 19.7 | 15.6 | 11.2 | 8.8 | 32.0 |
| Dipropylene glycol dimethyl ether (Proglyme) | 15.5 | 4.6 | 6.1 | 7.1 | 10.4 |
| N-Methylpyrrolidone | 16.8 | 2.8 | 6.7 | 8.2 | 32.8 |

Suitable aprotic solvents are aromatic hydrocarbons, aliphatic hydrocarbons, ethers, esters (including cyclic esters), amides (including cyclic amides), nitriles, acetals or mixtures thereof.

Examples of aromatic hydrocarbons are benzene, biphenyl, o-terphenyl, m-terphenyl, naphthalene, C$_1$-C$_{20}$-alkyl-monosubstituted or -polysubstituted aromatic hydrocarbons such as toluene, xylene, dodecylbenzene, tetradecylbenzene, hexadecylbenzene, methylnaphthalene, diisopropylnaphthalene, hexylnaphthalene or decylnaphthalene. Mixtures of the abovementioned aromatic hydrocarbons, in particular industrial aromatics mixtures as well, are also suitable.

Examples of aliphatic hydrocarbons are saturated or unsaturated C$_5$-C$_{40}$-hydrocarbons, in particular C$_{10}$-C$_{40}$-hydrocarbons, which are branched, cyclic or linear, such as n-tetradecane, n-pentadecane, n-hexadecane, n-heptadecane, n-octadecane, n-nonadecane, n-eicosane, n-heneicosane, n-docosane, n-tricosane, n-tetracosane, n-pentacosane, n-hexacosane, n-heptacosane, n-octacosane, mineral oils or high-pressure-hydrogenated mineral oils (known as white oils). Mixtures of the abovementioned aliphatic hydrocarbons are also suitable.

Examples of esters are C$_1$-C$_{40}$-alkyl esters of C$_2$-C$_{40}$-alkanoic acids, esters of C$_6$-C$_{24}$-alcohols with aromatic carboxylic acids, esters of C$_2$-C$_{12}$-dicarboxylic acids with linear or branched alcohols having from 1 to 22 carbon atoms or esters of C$_2$-C$_{40}$-alkanoic acids with polyols having from 2 to 10 carbon atoms and from 2 to 6 hydroxyl groups. These include C$_1$-C$_{40}$-alkyl esters of C$_8$-C$_{40}$-alkanoic acids or C$_6$-C$_{40}$-alkyl esters of C$_2$-C$_{40}$-alkanoic acids. Further examples of esters are esters of linear C$_6$-C$_{24}$-fatty acids with linear C$_3$-C$_{24}$-alcohols, esters of branched C$_6$-C$_{13}$-carboxylic acids with linear C$_6$-C$_{24}$-fatty alcohols, esters of linear C$_6$-C$_{24}$-fatty acids with branched alcohols, in particular 2-ethylhexanol.

Monoesters of fatty acids with alcohols having from 3 to 24 carbon atoms are of importance. This group of substances is made up of the products of the esterification of fatty acids having from 8 to 24 carbon atoms, for example caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, arachidic acid, gadoleic acid, behenic acid and erucic acid and also industrial mixtures thereof which are obtained, for example, in the pressure dissociation of natural fats and oils, in the reduction of aldehydes from the Roelen oxo process or the dimerization of unsaturated fatty acids, with alcohols such as isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachyl alcohol, gadoleyl alcohol, behenyl alcohol, erucyl alcohol and brassidyl alcohol and also industrial mixtures thereof which are obtained, for example, in the high-pressure hydrogenation of industrial methyl esters based on fats and oils or aldehydes from the Roelen oxo process and also as monomer fraction in the dimerization of unsaturated fatty alcohols.

Examples of dialkyl alkanedioates are di-C$_2$-C$_{32}$-alkyl esters of C$_4$-C$_{32}$-alkanedioic acids, preferably di-C$_2$-C$_{18}$-alkyl esters of C$_6$-C$_{16}$-alkanedioic acids. Particularly suitable dialkyl alkanedioates are dibutyl succinate, dibutyl adipate and dibutyl phthalate, in particular dibutyl adipate.

Esters of linear and/or branched fatty acids with polyhydric alcohols (e.g. propylene glycol, dimer diol or trimer triol) or triglycerides based on C$_6$-C$_{18}$-fatty acids, e.g. vegetable oils, are also suitable.

Esters also include cyclic esters such as gamma-butyrolactone and delta-valerolactone.

Examples of amides are N,N-di-C$_1$-C$_{12}$-alkyl-C$_8$-C$_{22}$-alkylamides such as N,N-dimethyldecanamide or N,N-dimethyldodecanamide.

Cyclic amides are, for example, N-methylpyrrolidone, caprolactam, dimethylethyleneurea and/or dimethylpropyleneurea.

Examples of ethers are dialkyl ethers, alkyl aryl ethers, diaryl ethers and polyol polyethers. Dialkyl ethers are linear or branched, symmetrical or unsymmetrical dialkyl ethers having a total of from 12 to 36 carbon atoms, in particular from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyldecyl ether, tert-butyl n-octyl ether, isopentyl n-octyl ether and 2-methylpentyl n-octyl ether.

Preference is also given to polyol polyethers such as diethylene glycol dimethyl ether (diglyme), dipropylene glycol dimethyl ether (proglyme).

Alkyl ethers of glycol acetates, e.g. 2-methoxyethyl acetate, 2-ethoxyethyl acetate, 2-butoxyethyl acetate and 1-methoxy-2-propyl acetate, are also suitable.

A suitable acetal is anisacetal (p-(dimethoxymethyl)anisole).

Particularly preferred aprotic solvents are dialkyl alkanedioates and polyol polyethers, in particular dipropylene glycol dimethyl ether.

The composition of the invention comprises at least one, in particular precisely one, ionic liquid.

The melting point of the ionic liquid at atmospheric pressure is preferably less than 100° C., preferably less than 50° C. and in particular less than 20° C.

As is known, ionic liquids consist of organic cations and organic or inorganic anions.

Possible organic cations are all cations as are customarily used in ionic liquids. The organic cations are preferably selected from among quaternary ammonium, oxonium, sulfonium and phosphonium cations and also from among uronium, thiouronium and guanidinium cations in which the single positive charge is delocalized over a plurality of heteroatoms.

Particular preference is given to using quaternary ammonium cations and very particular preference is given to using heterocyclic quaternary ammonium cations.

In particular, the heterocyclic quaternary ammonium cations are selected from among pyrrolium, imidazolium, 1H-pyrazolium, 3H-pyrazolium, 4H-pyrazolium, 1-pyrazolinium, 2-pyrazolinium, 3-pyrazolinium, 2,3-dihydroimidazolinium, 4,5-dihydroimidazolinium, 2,5-dihydroimidazolinium, pyrrolidinium, 1,2,4-triazolium (quaternary nitrogen atom in the 1 position), 1,2,4-triazolium (quaternary nitrogen atom in the 4 position), 1,2,3-triazolium (quaternary nitrogen atom in the 1 position), 1,2,3-triazolium (quaternary nitrogen atom in the 4 position), oxazolium, isoxazolium, thiazolium, isothiazolium, pyridinium, pyridazinium, pyrimidinium, piperidinium, morpholinium, pyrazinium, indolium, quinolinium, isoquinolinium, quinoxalinium and indolinium cations.

The above-described organic cations are species which are known per se and are described in detail in, for example, the German patent applications DE 10 2005 055 815 A, page 6, paragraph [0033], to page 15, paragraph [0074], DE 10 2005 035 103 A1, page 3, paragraph [0014], to page 10, paragraph [0051], and DE 103 25 050 A1, the paragraph [0006] bridging pages 2 and 3 in conjunction with page 3, paragraph [0011], to page 5, paragraph [0020]. The indicated passages of the German patent applications is expressly incorporated by reference for the purposes of more detailed explanation of the present invention.

Suitable organic cations preferably comprise ammonium ions of the formula (II)

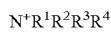

(II), where $R^1$, $R^2$, $R^3$ and $R^4$ are, independently of one another, alkyl radicals which may be substituted by heterofunctional groups and can form aliphatic ring systems with one another.

Preference is given to $R^1$, $R^2$, $R^3$ and $R^4$ being, independently of one another, alkyl and/or hydroxyalkyl. Particular preference is given to $R^1$, $R^2$, $R^3$ and $R^4$ being, independently of one another, $C_1$-$C_{20}$-alkyl and/or $C_1$-$C_{20}$-hydroxyalkyl. Very particular preference is given to $R^1$, $R^2$, $R^3$ and $R^4$ being, independently of one another, $C_1$-$C_8$-alkyl and/or $C_1$-$C_8$-hydroxyalkyl. Examples are tetrabutylammonium (TBA) or cholinium (N,N,N-trimethyl-N-hydroxyethylammonium).

In a further preferred embodiment, $R^1$, $R^2$, $R^3$ and $R^4$ are, independently of one another, alkyl radicals which may be substituted by heterofunctional groups and form aliphatic ring systems among one another. Examples are N,N-di-$C_1$-$C_{12}$-pyrrolidinium, 5-azaspiro[4.4]nonane or N,N-dimethylpyrrolidinium.

Suitable organic cations further comprise an imidazolium ion of the formula (III)

(III)

where $R^5$ is hydrogen or alkyl, $R^6$ is alkyl and $R^7$ is hydrogen or alkyl. The alkyl radical can be linear, cyclic or branched. Preference is given to $R^5$ being hydrogen or $C_1$-$C_{20}$-alkyl, $R^6$ being $C_1$-$C_{20}$-alkyl and $R^7$ being H or $C_1$-$C_6$-alkyl. Particular preference is given to $R^5$ being hydrogen or $C_1$-$C_6$-alkyl, $R^6$ being $C_1$-$C_6$-alkyl and $R^7$ being H or $C_1$-$C_6$-alkyl. $R^7$ is preferably H or methyl, in particular H. Examples are N-ethyl-N'-methylimidazolium (EMIM), N-methylimidazolium (MEHIM), N-butyl-N'-methylimidazolium (BMIM), N-ethyl-N'-ethylimidazolium (EEIM), N-n-propyl-N1-n-propylimidazolium (PPIM).

Suitable organic cations further comprise N-substituted pyridinium derivatives such as N-alkylpyridinium, where the alkyl radical is preferably a $C_1$-$C_{12}$-alkyl radical, in particular a $C_1$-$C_6$-alkyl radical.

Suitable organic cations further comprise N,N'-disubstituted pyrazolium derivatives such as an N,N'-dialkylpyrazolium derivative, where the alkyl radical is preferably a $C_1$-$C_{12}$-alkyl radical, in particular a $C_1$-$C_6$-alkyl radical. The dialkylpyrazolium derivative can optionally be substituted by a $C_1$-$C_4$-alkyl, for example 1,2,5-trimethylpyrazolium.

Suitable organic cations further comprise a guanidinium derivative such as guanidinium, hexamethylguanidinium, arginine cation or creatinium.

Among the above-described organic cations, use is made first and foremost of imidazolium cations, in particular the 1-ethyl-3-methylimidazolium cation (EMIM) or the 1-butyl-3-methylimidazolium cation (BMIM), in which the quaternary nitrogen is in each case located in the 1 position.

Possible inorganic and organic anions are all anions as are customarily used in ionic liquids. Examples of suitable anions are described in detail in the German patent applications DE 10 2005 055 815 A, page 2, paragraph [006] in conjunction with page 15, paragraph [0075], to page 17, paragraph [0088], and DE 103 25 050 A1, the paragraph [0006] bridging pages 2 and 3 in conjunction with page 5, paragraph [0021].

The indicated passages of the German patent applications are expressly incorporated by reference for the purposes of more detailed explanation of the present invention.

For example, the anion comprises a carboxylate, sulfonate, sulfate, phosphonate, phosphate, halogen, bis(trifluorosulfonyl)imide, aluminum tetrachloride, phosphorus fluoride (e.g. phosphorus hexafluoride) or dicyanimide, or a mixture thereof.

Preferred anions are carboxylates, sulfates, alkylsulfonates, halides (such as iodide or chloride), phosphonates, phosphates, bis(trifluorosulfonyl)imide or dicyanimide (2-cyanoguanidine). Particular preference is given to carboxylates, sulfates and alkylsulfonates, in particular alkylcarboxylates, polyether-comprising carboxylates, alkylsulfates and alkylsulfonates.

Suitable carboxylates are $C_1$-$C_{30}$-alkylcarboxylates, polyether-comprising carboxylates, arylcarboxylates and polycarboxylates.

Alkylcarboxylates are, for example, acetate, propionate, hexanoate, 2-ethylhexanoate, heptanoate, octanoate, isononanoate, decanoate, laurate, oleate, palmitate, stearate or octadecanoate.

Preferred polyether-comprising carboxylates correspond to the formula:

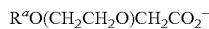

$$R^aO(CH_2CH_2O)CH_2CO_2^-$$

where n is an integer from 0 to 3 and $R^a$ is $C_1$-$C_{14}$-alkyl or $CH_2CO_2^-$. A suitable example is [2-(2-methoxyethoxy) ethoxy] acetate.

Preferred polycarboxylates are aliphatic dicarboxylates and tricarboxylates having from 2 to 32 carbon atoms, e.g. the anions of aconitic acid, adipic acid, citric acid, fumaric acid, glutaric acid, oxoglutaric acid, maleic acid, malic acid, malonic acid, oxalic acid, sebacic acid, succinic acid, tartaric acid.

Preferred arylcarboxylates are the anions of benzoic acid, cinnamic acid or hippuric acid.

Suitable alkylsulfonates are $C_1$-$C_{20}$-alkylsulfonates, in particular $C_1$-$C_{10}$-alkylsulfonates such as ethanesulfonate or octanesulfonate.

Suitable sulfates are those of the formula $R^c$—$OSO_3^-$, where $R^c$ is $C_1$-$C_{18}$-alkyl or $C_6$-$C_{12}$-aryl, preferably $C_1$-$C_8$-alkyl. A suitable example is ethylsulfate.

Suitable phosphates are $C_1$-$C_{10}$-dialkylphosphates such as dimethylphosphate or dibutylphosphate.

Suitable halides are chloride, bromide or iodide, preferably chloride.

Additional possibilities are the anions of free-radically polymerizable, olefinically unsaturated acids, preferably the anions of free-radically polymerizable acids comprising vinyl groups.

Examples of particularly suitable anions are the anions of acrylic acid, methacrylic acid, ethacrylic acid, chloroacrylic acid, cyanoacrylic acid, vinylacetic acid, vinylphosphonic acid, vinylsulfonic acid and vinylbenzene-2-, -3- and -4-sulfonic acid, in particular of acrylic acid and methacrylic acid.

The ionic liquids can be prepared by known methods, e.g. as described in Wasserscheid and Welton, Ionic liquids in synthesis, 2nd Edition, 2007, Wiley-VCH, or WO 2008/135482.

The ionic liquids can be composed of any combinations of the above-described organic cations and organic or inorganic anions, as long as the combination of a particular cation with a particular anion does not lead to undesirable chemical reactions or physical phase transformations such as the formation of precipitates or phase separation, which a person skilled in the art can, however, easily predict and therefore avoid on the basis of his general technical knowledge, optionally with the aid of a few orientating experiments.

Particularly suitable ionic liquids are tetrabutylammonium stearate, tetrabutylammonium [2-(2-methoxyethoxy) ethoxy]acetate, N-ethyl-N'-methylimidazolium chloride (EMIM Cl, e.g. Basionics ST 80), N-butyl-N'-methylimidazolium chloride (BMIM Cl, e.g. Basionics ST 70), N-ethyl-N'-methylimidazolium thiocyanate (EMIM SCN, e.g. Basionics VS 01), N-ethyl-N'-methylimidazolium tetrafluoroborate (EMIM $BF_4$, e.g. Basionics EE 03), N-ethyl-N'-methylimidazolium acetate (EMIM OAc, e.g. Basionics BC 01), N-ethyl-N'-methylimidazolium isononanoate, N-ethyl-N'-methylimidazolium octanoate, N-ethyl-N'-methylimidazolium methanesulfonate (EMIM $MeSO_3$, e.g. Basionics ST 35), N-ethyl-N'-methylimidazolium dicyanamide (EMIM DCA, e.g. Basionics VS 03), N-ethyl-N'-methylimidazolium diethylphosphate (EMIM DEP, e.g. Basionics LQ 11), N-ethyl-N'-methylimidazoliumtrifluoromethanesulfonate (EMIM Otf, e.g. Basionics VS 11), N-ethyl-N'-methylimidazolium bis(trifluoromethanesulfonyl)imide (EMIM TFSI, e.g. Basionics HP 01), tris(2-hydroxyethyl)methylammonium methylsulfate (MTEOA MeOSO3, e.g. Basionics FS 01), N-ethyl-N'-methylimidazolium dibutylphosphate, N-ethyl-N'-methylimidazolium ethylsulfate (EMIM $EtOSO_3$, e.g. Basionics LQ 01), N-butyl-N'-methylimidazolium acetate (BMIM acetate, e.g. Basionics BC02), N-ethyl-N'-ethylimidazolium propionate, N-propyl-N'-propylimidazolium acetate, cholinium octanoate and cholinium formate.

The composition of the invention preferably comprises at least 20% by weight, in particular at least 30% by weight, usually from 30 to 60% by weight, for example from 40 to 55% by weight, of inhibitor for the free-radical polymerization, based on the total weight of the components a), b) and c).

The weight ratio of aprotic solvent and ionic liquid in the composition of the invention is preferably in a range from 100:1 to 1:10, in particular from 90:10 to 60:40. Very particular preference is given to a ratio of aprotic solvent to ionic liquid of from 85:15 to 75:25.

The solubility of phenothiazine in the combination of the aprotic solvent and the ionic liquid is at least about as high as its weight average solubility. The weight average solubility can be calculated by multiplying the solubility of phenothiazine in the aprotic solvent by the proportion by weight of the aprotic solvent in the solvent combination and multiplying the solubility of the phenothiazine in the ionic liquid by the proportion by weight of the ionic liquid in the solvent combination and adding up the products. In some cases, there is advantageously a solubility-increasing effect, with the actual solubility being higher than the weight average solubility.

Furthermore, the combination of the components b), c) and phenothiazine has a lower viscosity than solutions of phenothiazine in only component c). This is particularly advantageous when the composition is mixed into monomers when a free-radical polymerization commences.

The production of the composition of the invention can, for example, be carried out by mixing the above-described components a), b) and c) with one another and then homogenizing the resulting mixture. From the point of view of methodology, this production process can be carried out using conventional and known apparatuses for mixing liquids or liquids and solids, e.g. stirred vessels, extruders, Ultraturrax, in-line dissolvers, homogenizing nozzles or countercurrent mixers.

The composition can comprise further inhibitors, e.g. phenolic inhibitors such as 4-methoxyphenol, 4-tert-butylcatechol, hydroquinone or 2,6-di-tert-butyl-4-methylphenol (Kerobit BHT), N-oxyl compounds such as 2,2,6,6-tetramethylpiperazin-1-oxyl (TEMPO), 4-hydroxy-2,2,6,6-tetramethylpiperazin-1-oxyl (HO-TEMPO) and 4-oxo-2,2,6,6-tetramethylpiperazin-1-oxyl (oxo-TEMPO), aromatic amines such as diphenylamine, para-phenylenediamine or para-phenylenediamine derivatives such as N,N'-di-sec-butyl-para-phenylenediamine (Kerobit BPD), or organic nitroso compounds or mixtures thereof.

Possible nitroxyl radicals (also referred to as N-oxyl radicals) are, in particular, those which are derived from a secondary amine which bears no hydrogen atoms on the α carbon atoms (i.e. the N-oxyl groups are derived from corresponding secondary amino groups). Among these, the N-oxyl radicals which are mentioned in EP-A 135280, the earlier application DE-A 19651307, U.S. Pat. No. 5,322,912, U.S. Pat. No. 5,412,047, U.S. Pat. No. 4,581,429, DE-A 1618141, CN-A 1052847, U.S. Pat. No. 4,670,131, U.S. Pat. No. 5,322,960, the earlier application DE-A 19602538, EP-A 765856 and JP-A 5/320217 are particularly suitable.

Suitable, stable N-oxyl radicals of this type which are derived from a secondary amine are, for example, those of the formula (IV):

(IV)

where $R^1$, $R^2$, $R^5$ and $R^6=$ identical or different straight-chain or branched, optionally substituted alkyl groups and $R^3$ and $R^4=$ identical or different straight-chain or branched, optionally substituted alkyl groups or $R^3CNCR^4=$ an optionally substituted cyclic structure.

Suitable compounds IV are, in particular, those which are mentioned in EP-A 135 280, the earlier application DE-A 19651307, U.S. Pat. No. 5,322,912, U.S. Pat. No. 5,412,047, U.S. Pat. No. 4,581,429, DE-A 16 18 141, CN-A 1052847, U.S. Pat. No. 4,670,131, U.S. Pat. No. 5,322,960 and the earlier application DE-A 19602538.

Examples of these are the stable N-oxyl radicals of the general formula (IV) in which $R^1$, $R^2$, $R^5$ and $R^6$ are (identical or different) $C_1$-$C_4$-alkyl groups such as methyl, ethyl, n-propyl, isopropyl, n-butyl, isobutyl or tert-butyl, linear or branched pentyl, phenyl or substituted groups thereof and $R^3$ and $R^4$ are (identical or different) $C_1$-$C_4$-alkyl groups such as methyl, ethyl, n-propyl, isopropyl, n-butyl, isobutyl or tert-butyl, linear or branched pentyl, substituted groups thereof or together with CNC are the cyclic structure

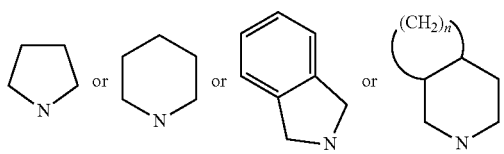

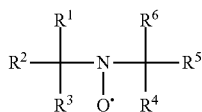

where n is an integer of from 1 to 10 (frequently from 1 to 6), including substituted cyclic structures of this type. Illustrated representatives are 2,2,6,6-tetramethyl-1-oxylpiperidine, 2,2,5,5-tetramethyl-1-oxylpyrrolidine and 4-oxo-2,2,6,6-tetramethyl-1-oxylpiperidine.

The N-oxyl radicals (IV) can be prepared from the corresponding secondary amines by oxidation, e.g. using hydrogen peroxide. In general, they can be prepared as pure substance.

Suitable N-oxyl radicals (IV) include, in particular, piperidin- or pyrrolidin-N-oxyls and di-N-oxyls of the general formulae (V) to (XII) below:

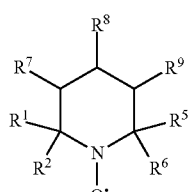

(V)

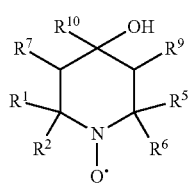

(VI)

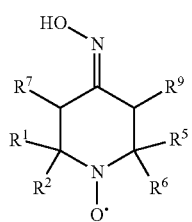

(VII)

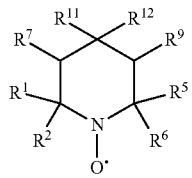

(VIII)

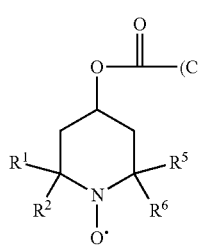

(IX)

-continued

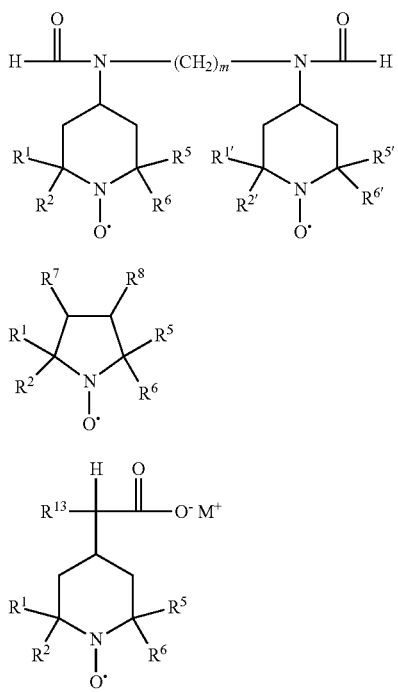

where
m=
2 to 10,
$R^7$, $R^8$, $R^9$=
independently of one another

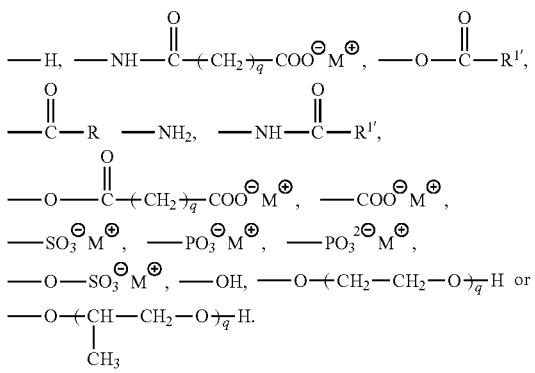

$M^\oplus$=
a hydrogen ion or an alkali metal ion,
q=
an integer from 1 to 10,
$R^1$, $R^2$, $R^5$, $R^6$=
independently of one another and independently of $R^1$, $R^2$, $R^5$, $R^6$ the same groups as $R^1$,
$R^{10}$=
$C_1$-$C_4$-alkyl, —CH=$CH_2$, —C≡CH, —CN,

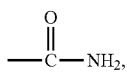

—COO$^\ominus$M$^\oplus$, —COOCH$_3$ or —COOC$_2$H$_5$, $R^{11}$=
an organic radical having at least one primary, secondary (e.g. —NHR$^1$) or tertiary amino group (e.g. —NR$^1$R$^2$) or at least one ammonium group —N$^\oplus$R$^{14}$R$^{15}$R$^{16}$X$^\ominus$, where X$^\ominus$=F$^\ominus$, Cl$^\ominus$, Br$^\ominus$, HSO$_4^\ominus$, SO$_4^{2\ominus}$, H$_2$PO$_4^\ominus$, HPO$_4^{2\ominus}$ or PO$_4^{3\ominus}$ and $R^{14}$, $R^{15}$, $R^{16}$ are, independently of one another, organic radicals (e.g. independently of one another and independently of $R^1$ the same groups as $R^1$),
$R^{12}$=
independently of $R^{11}$ the same groups as $R^{11}$ or —H, —OH, $C_1$-$C_4$-alkyl, —COO$^\ominus$M$^\oplus$, —C≡CH,

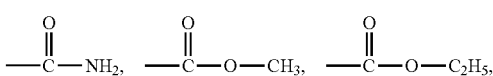

or hydroxy-substituted $C_1$-$C_4$-alkyl (e.g. hydroxyethyl or hydroxypropyl) or $R^{11}$, $R^{12}$=
together the oxygen of a carbonyl group and
$R^{13}$=—H, —CH$_3$ or —CH$_2$—$\overset{O}{\underset{\|}{C}}$—O$^\ominus$M$^\oplus$.

Preference is given to $R^1$=$R^2$=$R^5$=$R^6$=$R^{1'}$=$R^{2'}$=$R^{5'}$=$R^{6'}$=—CH$_3$.

As illustrated representatives of suitable N-oxyl radicals, mention may be made of 4-hydroxy-2,2,6,6-tetramethyl-1-oxylpiperidine, 4-hydroxy-2,6-diphenyl-2,6-dimethyl-1-oxylpiperidine, 4-carboxy-2,2,6,6-tetramethyl-1-oxylpiperidine, 4-carboxy-2,6-diphenyl-2,6-dimethyl-1-oxylpiperidine, 3-carboxy-2,2,5,5-tetramethyl-1-oxylpyrrolidine, 3-carboxy-2,5-diphenyl-2,5-dimethyl-1-oxylpyrrolidine, 4-acetyl-2,2,6,6-tetramethyl-1-oxylpiperidine, N,N'-bis(1-oxyl-2,2,6,6-tetramethylpiperidin-4-yl)-N,N'-bisformyl-1,6-diaminohexane and bis(1-oxyl-2,2,6,6-tetramethylpiperidin-4-yl) adipate.

The preparation of 3-carboxy-2,2,5,5-tetramethyl-1-oxylpyrrolidine is described, for example, in Romanelli, M.; Ottaviani, M. F.; Martini, G.; Kevan, L., JPCH J: Phys. Chem., EN, 93, 1, 1989, pp. 317-322.

The compounds (IX) and (X) can be obtained as described in U.S. Pat. No. 4,665,185 (e.g. example 7) and DE-A 19510184.

Further suitable illustrated representatives are:

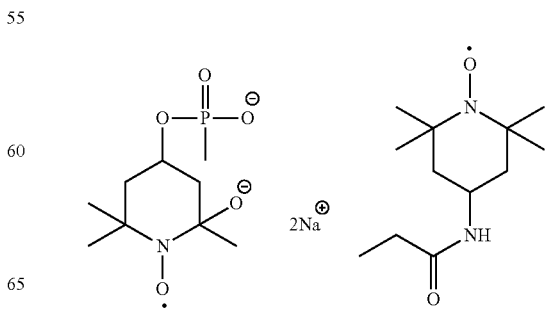

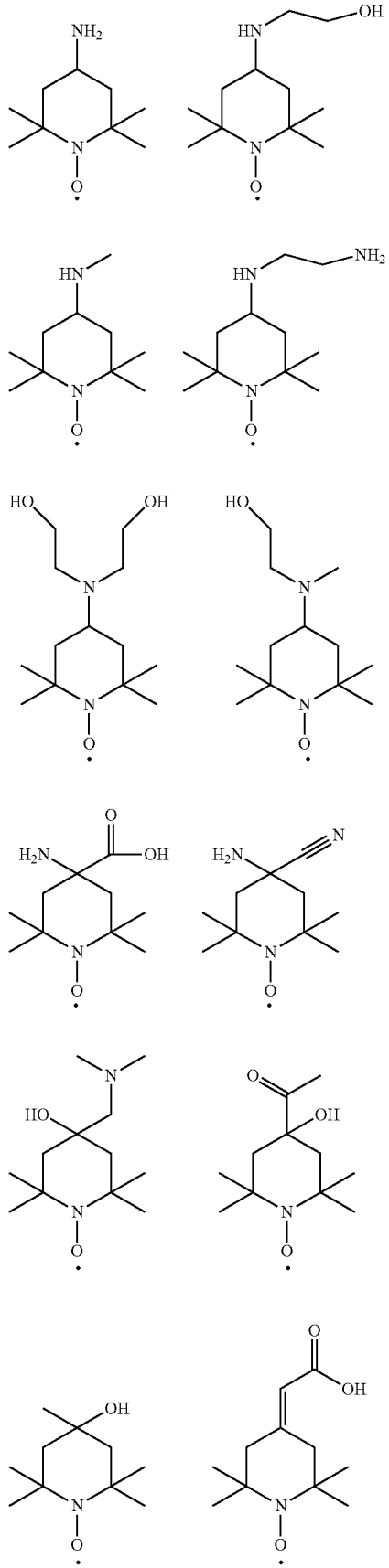
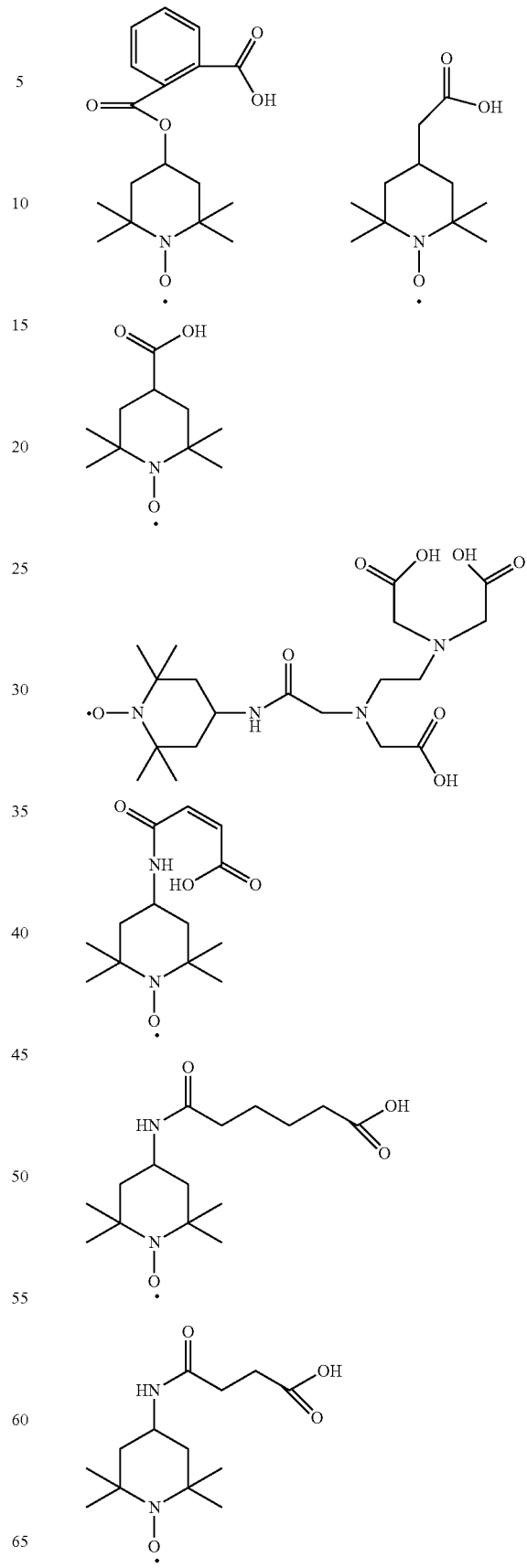

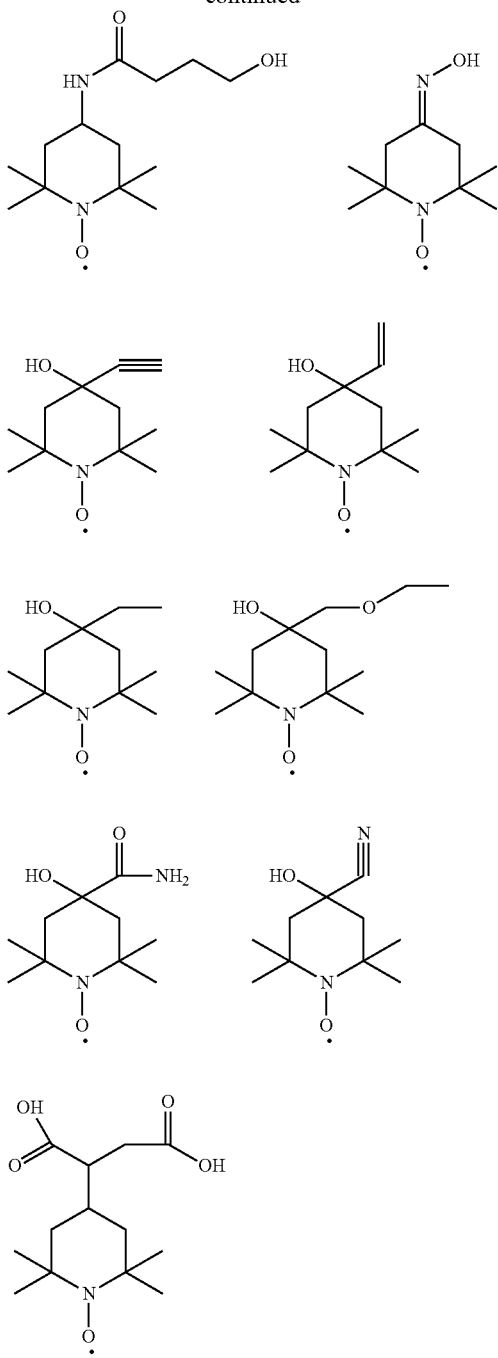

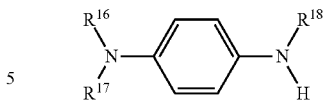

Suitable organic nitroso compounds are, for example, N-nitrosoarylamines or nitroso compounds having the nitroso group bound directly to a carbon atom of an aromatic ring. Examples which may be mentioned are nitrosophenols such as 4-nitrosophenol, nitrosonaphthols such as 2-nitroso-1-naphthol, nitrosobenzene, N-nitroso-N-methylurea, nitroso-N,N-dialkylanilines where alkyl=methyl, ethyl, propyl and/or butyl, N-nitrosodiphenylamine, N-nitrosophenylnaphthylamine, 4-nitrosodinaphthylamine and p-nitrosodiphenylamine.

Suitable p-phenylenediamines are those of the general formula (XIII)

(XIII)

where $R^{16}$, $R^{17}$, $R^{18}$=independently of one another alkyl, aryl, alkaryl or aralkyl having up to 20 carbon atoms, or hydrogen.

Particularly suitable compounds (XIII) are those in which $R^{16}$, $R^{17}$, $R^{18}$=independently of one another methyl, ethyl, propyl, isopropyl, isobutyl, sec-butyl, n-butyl, pentyl, phenyl or naphthyl. As examples of suitable compounds XIII, mention may be made of: N,N'-bis-sec-butyl-p-phenylenediamine, N-phenyl-N'-isopropylphenylenediamine, N-naphthyl-N'-sec-butyl-p-phenylenediamine, N,N,N'-trimethyl-p-phenylenediamine, N,N,N'-triethyl-p-phenylenediamine, N,N-dimethyl-p-phenylenediamine, N,N-diethyl-p-phenylenediamine, N-phenyl-N',N'-dimethyl-p-phenylenediamine, N-phenyl-N',N'-diethyl-p-phenylenediamine, N-phenyl-N',N'-dipropyl-p-phenylenediamine, N-phenyl-N',N'-di-n-butyl-p-phenylenediamine, N-phenyl-N',N'-di-sec-butyl-p-phenylenediamine, N-phenyl-N'-methyl-N'-ethyl-p-phenylenediamine, N-phenyl-N'-methyl-N'-propyl-p-phenylenediamine, N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-butyl-p-phenylenediamine, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine and p-phenylenediamine.

It is naturally also possible to use mixtures of all the various abovementioned polymerization inhibitors in addition to phenothiazine.

The type and amount of these further constituents depend on the purpose for which the composition is used.

The composition of the invention is used in the stabilization of free-radically polymerizable monomers against free-radical polymerization.

Free-radically polymerizable monomers are, for example, vinyl monomers of the general formula XIV

where X is a hydrogen atom, a halogen atom, a carboxyl group, a sulfonic acid group (—$SO_3H$), a phosphonic acid group (—$PO_3H_2$), a silane group (—$SiH_3$) or a monovalent to decavalent, preferably monovalent to hexavalent and more preferably monovalent to trivalent, organic or metal-organic radical and Y is a hydrogen atom, a halogen atom, a nitrile group, an alkyl group having from 1 to 20 carbon atoms, a cycloalkyl group having from 3 to 20 carbon atoms or an aryl group having from 6 to 22 carbon atoms.

In the general formula XIV, the index n is an integer from 1 to 10, preferably from 1 to 6 and more preferably from 1 to 3. In particular, n is 1.

The radical X is a hydrogen atom, a halogen atom, a carboxyl group, a sulfonic acid group (—$SO_3H$), a phosphonic acid group (—$PO_3H_2$), a silane group (—$SiH_3$) or a monovalent to decavalent, preferably monovalent to hexavalent and more preferably monovalent to trivalent, organic or metal-organic radical. In particular, it is a monovalent organic radical.

For the purposes of the present invention, an organic radical is a radical which comprises at least one carbon atom.

For the purposes of the present invention, a metal-organic radical is a radical which comprises at least one carbon atom and also at least one silicon atom and/or at least one boron atom, in particular at least one silicon atom.

The organic radical and the metal-organic radical can be of low molecular weight, oligomeric or polymeric. "Low molecular weight" means that the radical concerned is made up of one structural unit or two identical or different structural units. "Oligomeric" means that the radical concerned is made up of from 2 to 12 identical or different structural units. "Polymeric" means that the radical concerned is made up of more than 12 identical or different structural units.

The structural units of the organic radical and of the metal-organic radical can comprise at least one heteroatom, preferably selected from the group consisting of oxygen, sulfur, nitrogen, phosphorus, fluorine, chlorine and bromine, more preferably oxygen, sulfur and phosphorus, in particular oxygen.

Particular preference is given to the vinyl monomers of the general formula XIV, in which n is 1 and X is a hydrogen atom, a halogen atom, a sulfonic acid group, a phosphonic acid group, a silane group (—SiH$_3$) or a monovalent organic or metal-organic radical. Monomers of this type are also referred to as vinyl monomers in the narrower sense (cf. Römpp Online 2007, "Vinylmonomere").

Examples of well-suited halogen atoms X are fluorine, chlorine and bromine, in particular chlorine.

Examples of well-suited monovalent organic radicals X are alkyl radicals R which preferably have from 1 to 12, more preferably from 1 to 10 and in particular from 1 to 8, carbon atoms, cycloalkyl radicals R which preferably have from 3 to 10, more preferably from 4 to 8 and in particular 5 or 6, carbon atoms, aryl radicals R which preferably have from 6 to 22, more preferably from 6 to 16 and in particular from 6 to 10, carbon atoms, alkyl, cycloalkyl and aryl ether radicals (—OR), where the radical R is preferably selected from the group consisting of the abovementioned alkyl radicals, cycloalkyl radicals and aryl radicals R, nitrile group (—CN), carboxyl group (—COOH), carboxylalkyl ester radicals (—O—CO—R or —CO—O—R) which preferably have from 1 to 10, more preferably from 1 to 8 and in particular from 1 to 6, carbon atoms in the alkyl radical R, carboxylcycloalkyl ester radicals (—O—CO—R or —CO—O—R) which preferably have from 3 to 10, more preferably from 4 to 8 and in particular 5 or 6 carbon atoms in the cycloalkyl radical R, carboxylaryl ester radicals (—O—CO—R or —CO—O—R) which preferably have from 6 to 22, more preferably from 6 to 16 and in particular from 6 to 10, carbon atoms in the aryl radical R, carboxylamide radical (—CO—NH$_2$), carboxylamide radicals (—CO—NRH or —CO—NR$_2$) which are substituted on the nitrogen by at least one radical R which is preferably selected from the group consisting of the abovementioned alkyl radicals, cycloalkyl radicals and aryl radicals R, where two radicals R can also be cyclically joined to one another, carboxylamide radicals (—NR—CO—R), where the radical R is preferably selected from the group consisting of the abovementioned alkyl radicals, cycloalkyl radicals and aryl radicals R and the hydrogen atom, or where the two radicals R are cyclically joined to one another so as to preferably result in a four-, five- or six-membered ring and amino radicals (—NHR or —NR$_2$) which are substituted on the nitrogen atom by at least one radical which is preferably selected from the group consisting of the abovementioned alkyl radicals, cycloalkyl radicals and aryl radicals R, where two radicals R can also be cyclically joined to one another, where the radicals R can be substituted or unsubstituted.

Examples of well-suited substituents for the substituted radicals R are halogen atoms, preferably fluorine, chlorine and bromine, in particular fluorine and chlorine, nitrile groups, nitro groups, carboxyl groups, sulfonic acid groups, ether radicals (—OR), ester radicals (—O—CO—R or —CO—O—R), carboxylamide radicals (—NH—CO—R) and amino radicals (—NHR or —NR$_2$), in particular carboxyl groups and sulfonic acid groups. Here, the radicals R have the meanings indicated above.

Examples of well-suited monovalent metal-organic radicals X are silyl radicals (—SiH$_2$R, —SiHR$_2$ or —SiR$_3$), where the radical R is preferably selected from the group consisting of the abovementioned alkyl radicals, cycloalkyl radicals and aryl radicals R, where 2 or 3 radicals R can also be cyclically joined to one another, and silyl ether radicals (—SiH$_2$(OR), —SiH(OR)$_2$, —Si(OR)$_3$, —SiHR(OR), —SiR$_2$(OR), or —SiR(OR)$_2$), where the radical R is preferably selected from the group consisting of the abovementioned alkyl radicals R, cycloalkyl radicals and aryl radicals R, where 2 or 3 radicals R can also be cyclically joined to one another, where these silyl radicals and silyl ether radicals X can also be joined via an oxygen atom to the vinyl group.

In the general formula XIV, the variable Y is a hydrogen atom, a halogen atom, a nitrile group, an alkyl group having from 1 to 20 carbon atoms, a cycloalkyl group having from 3 to 20 carbon atoms or an aryl group having from 6 to 22 carbon atoms, preferably a hydrogen atom, a halogen atom, a nitrile group, a methyl group or ethyl group, in particular a hydrogen atom or a methyl group.

Well-suited vinyl monomers XIV come from the compound classes of 1-olefins, vinyl halides, vinylaromatics, vinyl ethers, vinyl esters, vinylamides, vinylsilanes, vinyl silyl ethers, vinylsiloxanes, vinylamines, vinylamides, vinylsulfonic acid, vinylphosphonic acid, vinylcarboxylic acids, vinylaromaticsulfonic acids, acrylic acids, acrylic esters, acrylamides, acrylonitriles, allyl ethers and allyl esters.

Particularly well-suited vinyl monomers XIV come from the compound classes of 1-olefins, vinyl halides, vinylaromatics, vinyl ethers, vinyl esters, vinylamides, vinylsulfonic acid, vinylphosphonic acid, vinylcarboxylic acids, vinylaromaticsulfonic acids, acrylic acids, acrylic esters, acrylamides and acrylonitriles.

Examples of particularly well-suited 1-olefins are ethylene, propene, 1-butene, 1-pentene and 1-hexene.

Examples of particularly well-suited vinyl halides are vinyl fluoride, vinyl chloride and vinyl bromide.

Examples of particularly well-suited vinylaromatics are styrene and alpha-methylstyrene.

Examples of particularly well-suited vinyl ethers are vinyl methyl ether, vinyl ethyl ether, vinyl propyl ether and vinyl butyl ether.

Examples of particularly well-suited vinyl esters are vinyl acetate and vinyl propionate.

Examples of particularly well-suited vinylamides are N-vinylformamide, N-vinylacetamide, N-vinylpyrrolidone and N-vinylcaprolactam.

An example of a particularly well-suited vinylcarboxylic acid is vinylacetic acid.

Examples of particularly well-suited vinylaromaticsulfonic acids are vinylbenzene-2-, -3- and -4-sulfonic acid.

Examples of particularly well-suited acrylic acids are acrylic acid, methacrylic acid, ethacrylic acid, chloroacrylic acid and cyanoacrylic acid, in particular acrylic acid and methacrylic acid.

Examples of particularly well-suited acrylic esters are methyl, ethyl, propyl, i-propyl, n-butyl, i-butyl, 1,1-diethylbutyl, 2-ethylhexyl, 1,1-diethylpropyl, 1-methyl-1-ethylpropyl, 1-methyl-1-ethylbutyl, 1,1-dimethylbutyl, 1,1-dimethylpropyl and tert-butyl acrylate and methacrylate, preferably methyl acrylate, ethyl acrylate, n-butyl acrylate (NBA), isobutyl acrylate (IBA), tert-butyl acrylate, 2-ethylhexyl acrylate (EHA), hydroxyalkyl acrylates such as 2-hydroxyethyl acrylate, 2-hydroxypropyl acrylate, 4-hydroxybutyl acrylate and 2-hydroxyethyl methacrylate and 2-hydroxypropyl methacrylate, tert-butyl methacrylate (TBMA) and 2-ethylhexyl methacrylate (MEHA).

Examples of particularly well-suited acrylamides are acrylamide and methacrylamide.

Examples of particularly well-suited acrylonitriles are acrylonitrile and methacrylonitrile.

The invention further provides a method for the immediate stopping of free-radical polymerizations, wherein the composition of the invention is added to a free-radically polymerizing system.

The composition of the invention is preferably used in a method for the inhibition of an uncontrolled free-radical polymerization of free-radically polymerizable monomers in a vessel. The commencement of an uncontrolled free-radical polymerization can be registered by detection of a temperature increase in the vessel or by detection of a particularly steep temperature increase gradient (when the temperature increase of the system per unit time is above a prescribed value). If the commencement of an uncontrolled free-radical polymerization is detected, the composition of the invention is introduced into the vessel and mixed in.

The vessel can be any vessel or any container which is suitable for containing free-radically polymerizable monomers, e.g. reaction vessels such as reactors or storage containers for storage. The abovementioned method is of particular importance for preventing the uncontrolled polymerization of acrylic acid in a reactor or storage container.

An incipient runaway reaction of monomers in the vessel can be detected in the course of process monitoring. Detection can be effected firstly by exceeding of staggered temperature thresholds, and secondly by undershooting of a time limit for the time of a temperature increase between two temperature thresholds. The temperature thresholds and the times are selected appropriately for the intended use. The most effective way of terminating the incipient runaway reaction is the addition of inhibitors for the free-radical polymerization. The inhibitors for the free-radical polymerization are, according to the invention, added as constituent of the above defined composition of the invention. In particular, the addition of the composition is effected by injection into the vessel in which the temperature increase was already detected in a first step of recognition of an emergency. The composition of the invention is added in an amount sufficient to stop the incipient, uncontrolled free-radical polymerization. It is usual to add such an amount of the composition of the invention that a final concentration of the inhibitor of from 50 to 1000 ppm is achieved. Preference is given to adding such an amount of the composition of the invention that a final concentration of the inhibitor of from 100 to 500 ppm is achieved and particular preference is given to adding such an amount of the composition of the invention that a final concentration of the inhibitor of from 125 to 250 ppm is achieved.

The invention is illustrated in detail by the accompanying figures and examples.

EXAMPLE 1

Figure 1:
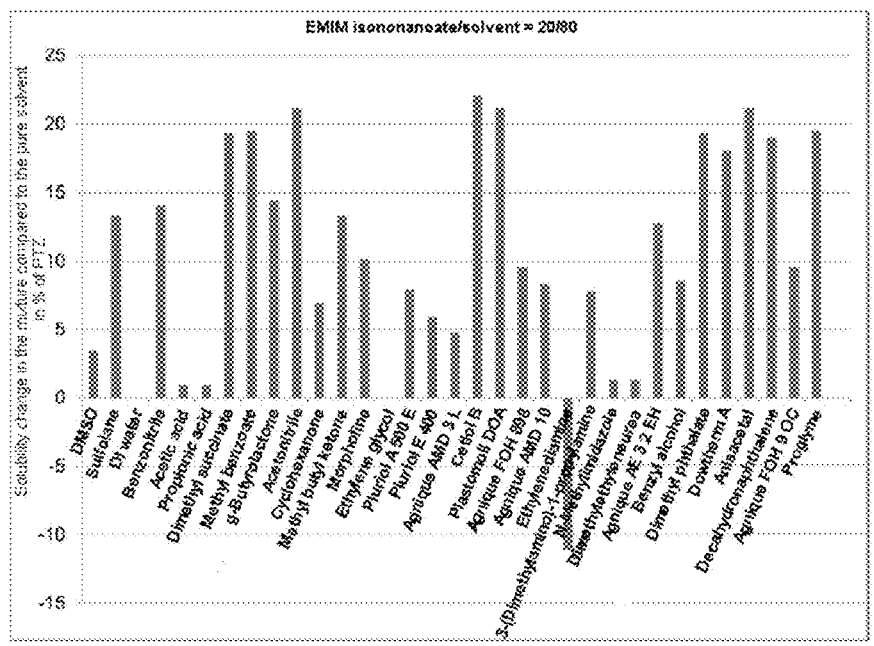
FIG. 1 is a bar chart which shows the relative solubility of phenothiazine in a mixture of EMIM isononanoate and solvent (weight ratio 20/80), based on the solubility of phenothiazine in the pure solvent.
Figure 2:
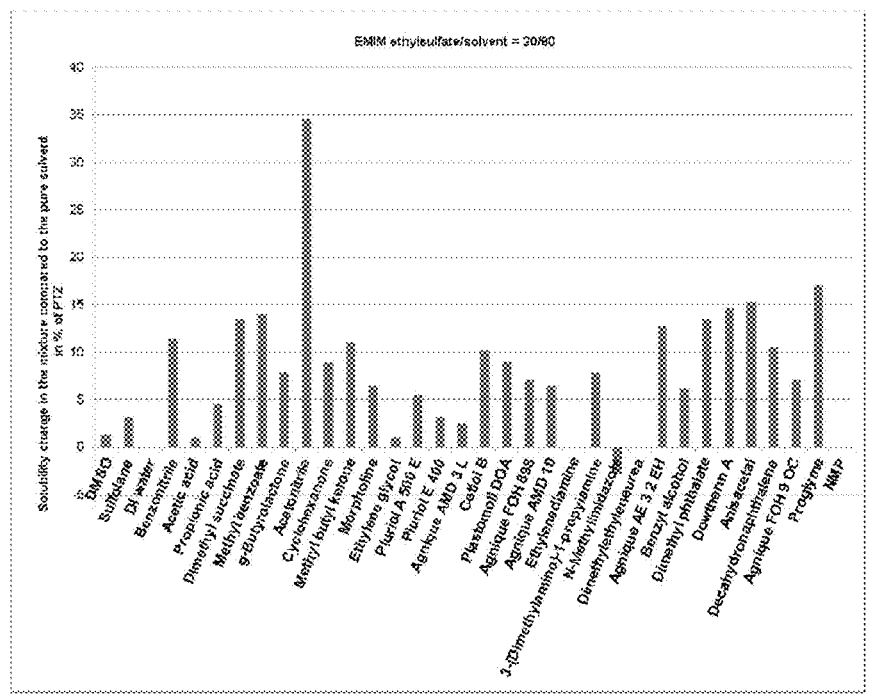
FIG. 2 is a bar chart which shows the relative solubility of phenothiazine in a mixture of EMIM ethylsulfate and solvent (weight ratio 20/80), based on the solubility of phenothiazine in the pure solvent.
Figure 3:
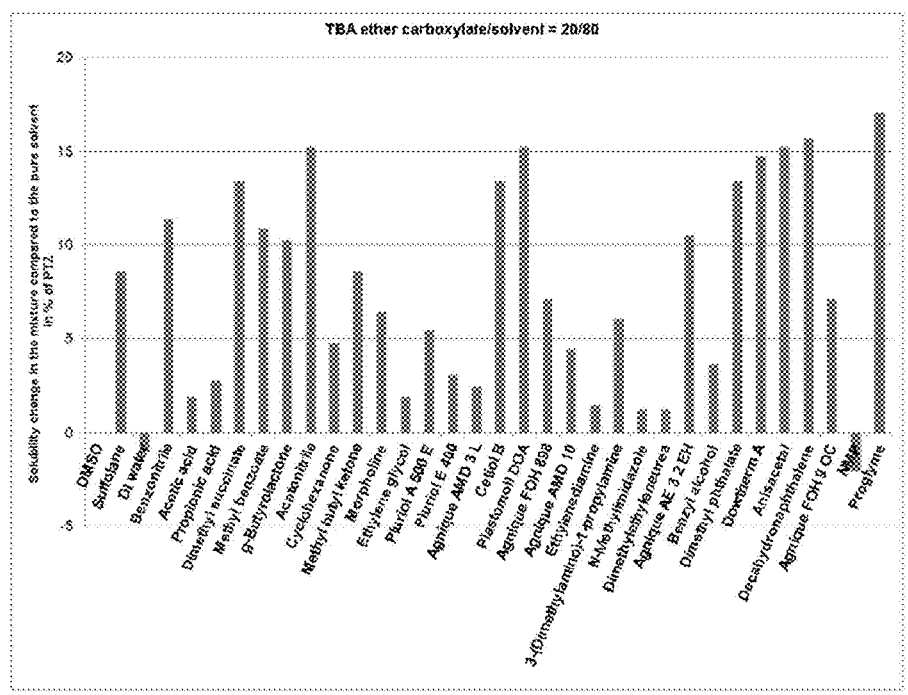
FIG. 3 is a bar chart which shows the relative solubility of phenothiazine in a mixture of TBA ether carboxylate and solvent (weight ratio 20/80), based on the solubility of phenothiazine in the pure solvent.
Figure 4:
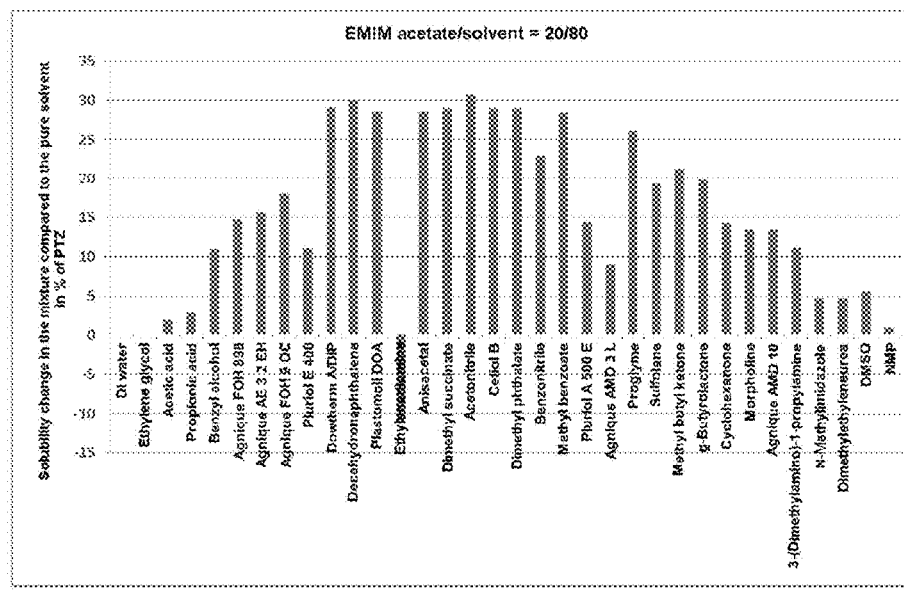
FIG. 4 is a bar chart which shows the relative solubility of phenothiazine in a mixture of EMIM acetate and solvent (weight ratio 20/80), based on the solubility of phenothiazine in the pure solvent.

In this example, the crystallization behavior of a solution of phenothiazine in a mixture of ionic liquid and solvent (weight ratio of ionic liquid/solvent=20/80) was examined. The compositions were stored for 14 days at −70° C. (dry ice) during the day and at −20° C. overnight and subsequently assessed visually at room temperature.

The samples which display no sediment or crystals after 14 days are evaluated as good. The following tables show the compositions and the results for phenothiazine in 4 different ionic liquids combined with different solvents.

TABLE 2

Crystallization tests for EMIM acetate/solvent mixtures (20/80) saturated with PTZ

| Solvent | EMIM acetate [%] | PTZ [%] | Assessment after 14 days |
|---|---|---|---|
| DMSO | 8.9 | 55.6 | Liquid |
| Benzonitrile | 12.5 | 37.5 | Liquid + sediment |
| Dimethyl succinate | 12.9 | 35.5 | Liquid + sediment |
| Methyl benzoate | 12.5 | 37.5 | Crystalline sediment, liquid |
| Acetonitrile | 12.9 | 35.5 | Liquid + crystals |
| Methyl butyl ketone | 11.8 | 41.2 | Liquid + sediment |
| Ethylenediamine | 13.3 | 33.3 | Liquid + crystals |
| N-Methylimidazole | 9.3 | 53.5 | Crystal slurry |
| Proglyme | 12.5 | 37.5 | Liquid |

TABLE 3

Crystallization tests for EMIM isononanoate/solvent mixtures (20/80) saturated with PTZ

| Solvent | EMIM isononanoate [%] | PTZ [%] | Assessment after 14 days |
|---|---|---|---|
| DMSO | 9.3 | 53.5 | Liquid |
| Methyl butyl ketone | 13.3 | 33.3 | Liquid + sediment |
| Ethylenediamine | 13.3 | 33.3 | Liquid + sediment |

TABLE 3-continued

Crystallization tests for EMIM isononanoate/solvent mixtures (20/80) saturated with PTZ

| Solvent | EMIM isononanoate [%] | PTZ [%] | Assessment after 14 days |
|---|---|---|---|
| N-Methylimidazole | 11.1 | 44.4 | Liquid |
| N-Methylimidazole | 10.0 | 50.0 | Liquid |
| Proglyme | 13.8 | 31.0 | Liquid |

TABLE 4

Crystallization tests for EMIM ethylsulfate/solvent mixtures (20/80) saturated with PTZ

| Solvent | EMIM ethylsulfate [%] | PTZ [%] | Assessment after 14 days |
|---|---|---|---|
| Acetonitrile | 12.1 | 39.4 | White sediment, liquid |
| Methyl butyl ketone | 13.8 | 31.0 | Yellow sediment, liquid |
| N-Methylimidazole | 10.8 | 45.9 | Crystals, liquid |
| N-Methylimidazole | 12.0 | 40.1 | Liquid |
| N-Methylimidazole | 11.0 | 45.1 | Liquid |
| Proglyme | 14.3 | 28.6 | Liquid |

TABLE 5

Crystallization tests for TBA ether carboxylate/solvent mixtures (20/80) saturated with PTZ

| Solvent | TBA ether carboxylate [%] | PTZ [%] | Assessment after 14 days |
|---|---|---|---|
| Methyl butyl ketone | 14.3 | 28.6 | White sediment, liquid |
| N-Methylimidazole | 12.0 | 40.1 | Liquid |
| N-Methylimidazole | 11.0 | 45.1 | Liquid |
| Dimethylethyleneurea | 12.0 | 40.1 | Crystalline sediment, liquid |
| Dimethylethyleneurea | 11.0 | 45.1 | Crystals, liquid |
| Proglyme | 14.3 | 28.6 | Liquid |

EXAMPLE 2

In this example, heating tests in acrylic acid (AA) were carried out. In this test, a sample of acrylic acid is maintained at 120° C. under an air atmosphere and the time until occurrence of turbidity in the solution is determined. The time is considered to be the inhibition period (IP) of the acrylic acid sample.

1. Production of Liquid Phases Admixed with Various Polymerization Inhibitors.

Freshly prepared pure acrylic acid (GAA, prepared as described in DE-A 102007055086) which had been polymerization-inhibited with, based on its weight, 200 ppm by weight of methoxyphenol (MEHQ) was freed of MEHQ under reduced pressure (1000 Pa) by means of double, successive distillation. The purity of the pure acrylic acid distillate RD produced in this way was >99.8% by weight, at a total aldehyde and ketone content of <5 ppm by weight, a diacrylic acid content of <1 ppm by weight and a propionic acid content of <200 ppm by weight.

A part 1 was taken from the pure acrylic acid distillate RD and a stock solution 1 comprising 1000 ppm by weight of phenothiazine (PTZ) was produced with stirring. Another part 2 of the pure acrylic acid distillate RD was mixed with different amounts of ionic liquids IL, solvents LM or mixtures IL/LM of ionic liquid IL with solvent LM to produce different stock solutions 2 in which, for example, different amounts of various ionic liquids IL, various solvents LM or various mixtures IL/LM of ionic liquid IL with solvent LM had been dissolved.

40 parts by weight of stock solution 1 were mixed with 960 parts by weight of the pure acrylic acid distillate RD so as to give the stock solution 3. Part of this stock solution 3 was divided into identical samples having volumes of 1 ml.

Samples taken from the stock solutions 2 were combined with the various 1 ml samples obtained from the stock solutions 3 in such a way that the desired compositions of acrylic acid, phenothiazine (PTZ), ionic liquids IL, solvents LM or mixtures IL/LM of ionic liquids IL with solvents LM were obtained by doping. The doped samples produced in this way were provided for further examination on the same day. For repeat measurements, fresh doped samples were produced in order to minimize the influence of the acrylic acid oligomers obtained by Michael oligomerization.

2. Examination of the Polymerization Tendency of the Doped Samples of the Various Liquid Phases P.

To examine the polymerization tendency of the respective doped sample, three HPLC vials (transparent vessels having a fill volume of 1.5 ml) were in each case charged with 0.5 ml of the respective sample under air and subsequently tightly closed by means of a crimped cap. Immediately after production, in each case up to 92 vials charged as described were hung in a holder made for this purpose and kept at a temperature of 120° C. in a convection drying oven while the holder rotated at six revolutions per minute in order to ensure complete mixing in the vials (the liquid content of the respective vial came into contact with the crimped cap six times per minute). The time T to complete polymerization of the respective sample in the associated vial was then measured. For this purpose, the samples in the vials in the drying oven were monitored by means of a digital video camera and the video film was subsequently evaluated visually.

Three associated values of T were determined in this way for each doped sample and these were arithmetically averaged. The resulting averages IP (in minutes) for the various samples, including their associated relevant contents of constituents other than acrylic acid, are listed below (the contents indicated are in each case based on the total mass comprised in the respective sample).

When mixtures of ionic liquid and solvent were used as additive, the weight ratio of ionic liquid to solvent or to the solvent mixture (IL/LM) was 20/80.

TABLE 6

Inhibiting periods for stabilized mixtures of AA with phenothiazine and solvent or phenothiazine and ionic liquid or phenothiazine and ionic liquid and solvent.

| Additive | | Inhibitor | | Inhibiting |
|---|---|---|---|---|
| LM, IL or IL/LM | Concentration ppm | Compound | Concentration ppm | period min |
| — | — | — | — | 240 min |
| DMSO | 1000 ppm | PTZ | 20 ppm | 317 min |
| Sulfolane | 1000 ppm | PTZ | 20 ppm | 330 min |
| DI water | 1000 ppm | PTZ | 20 ppm | 327 min |
| Benzonitrile | 1000 ppm | PTZ | 20 ppm | 334 min |
| Acetic acid | 1000 ppm | PTZ | 20 ppm | 347 min |
| Propionic acid | 1000 ppm | PTZ | 20 ppm | 337 min |
| Dimethyl succinate | 1000 ppm | PTZ | 20 ppm | 348 min |
| Methyl benzoate | 1000 ppm | PTZ | 20 ppm | 350 min |
| g-Butyrolactone | 1000 ppm | PTZ | 20 ppm | 361 min |
| Acetonitrile | 1000 ppm | PTZ | 20 ppm | 335 min |
| Cyclohexanone | 1000 ppm | PTZ | 20 ppm | 75 min |
| Methyl butyl ketone | 1000 ppm | PTZ | 20 ppm | 309 min |
| Morpholine | 1000 ppm | PTZ | 20 ppm | 410 min |
| Ethylene glycol | 1000 ppm | PTZ | 20 ppm | 365 min |
| Pluriol A 500 E | 1000 ppm | PTZ | 20 ppm | 320 min |
| Pluriol E 400 | 1000 ppm | PTZ | 20 ppm | 292 min |
| Agnique AMD 3 L | 1000 ppm | PTZ | 20 ppm | 405 min |
| Cetiol B | 1000 ppm | PTZ | 20 ppm | 347 min |
| Plastomoll DOA | 1000 ppm | PTZ | 20 ppm | 350 min |
| Agnique FOH 898 | 1000 ppm | PTZ | 20 ppm | 332 min |
| Agnique AMD 10 | 1000 ppm | PTZ | 20 ppm | 335 min |
| Ethylenediamine | 1000 ppm | PTZ | 20 ppm | 341 min |
| 3-(Dimethylamino)-1-propylamine | 1000 ppm | PTZ | 20 ppm | 407 min |
| N-Methylimidazole | 1000 ppm | PTZ | 20 ppm | 366 min |
| Dimethylethyleneurea | 1000 ppm | PTZ | 20 ppm | 313 min |
| Agnique AE 3 2 EH | 1000 ppm | PTZ | 20 ppm | 279 min |
| Benzyl alcohol | 1000 ppm | PTZ | 20 ppm | 355 min |
| Dimethyl phthalate | 1000 ppm | PTZ | 20 ppm | 348 min |
| Dowtherm A | 1000 ppm | PTZ | 20 ppm | 323 min |
| Anisacetal | 1000 ppm | PTZ | 20 ppm | 320 min |
| Decahydronaphthalene | 1000 ppm | PTZ | 20 ppm | 347 min |
| Agnique FOH 9 OC | 1000 ppm | PTZ | 20 ppm | 255 min |
| Proglyme | 1000 ppm | PTZ | 20 ppm | 339 min |
| NMP | 1000 ppm | PTZ | 20 ppm | 343 min |
| EMIM acetate | 1000 ppm | PTZ | 20 ppm | 296 min |
| EMIM acetate/DMSO | 1000 ppm | PTZ | 20 ppm | 378 min |
| EMIM acetate/benzonitrile | 1000 ppm | PTZ | 20 ppm | 416 min |
| EMIM acetate/dimethyl succinate | 36 ppm | PTZ | 20 ppm | 372 min |
| EMIM acetate/gamma-butyrolactone | 1000 ppm | PTZ | 20 ppm | 414 min |
| EMIM acetate/acetonitrile | 1000 ppm | PTZ | 20 ppm | 411 min |
| EMIM acetate/methyl butyl ketone | 29 ppm | PTZ | 20 ppm | 351 min |
| EMIM acetate/ethylenediamine | 1000 ppm | PTZ | 20 ppm | 356 min |
| EMIM acetate/3-(dimethylamino)-1-propylamine | 25 ppm | PTZ | 20 ppm | 422 min |
| EMIM acetate/N-methylimidazole | 1000 ppm | PTZ | 20 ppm | 451 min |
| EMIM acetate/proglyme | 33 ppm | PTZ | 20 ppm | 395 min |
| EMIM isononanoate | 1000 ppm | PTZ | 20 ppm | 379 min |
| EMIM isononanoate/DMSO | 1000 ppm | PTZ | 20 ppm | 373 min |
| EMIM isononanoate/g-butyrolactone | 33 ppm | PTZ | 20 ppm | 368 min |
| EMIM isononanoate/methyl butyl ketone | 40 ppm | PTZ | 20 ppm | 382 min |
| EMIM isononanoate/ethylenediamine | 1000 ppm | PTZ | 20 ppm | 416 min |
| EMIM isononanoate/3-(dimethylamino)-1-propylamine | 1000 ppm | PTZ | 20 ppm | 575 min |
| EMIM isononanoate/N-methylimidazole | 1000 ppm | PTZ | 20 ppm | 469 min |

TABLE 6-continued

Inhibiting periods for stabilized mixtures of AA with phenothiazine and solvent or phenothiazine and ionic liquid or phenothiazine and ionic liquid and solvent.

| LM, IL or IL/LM | Additive Concentration ppm | Inhibitor Compound | Inhibitor Concentration ppm | Inhibiting period min |
|---|---|---|---|---|
| EMIM isononanoate/proglyme | 44 ppm | PTZ | 20 ppm | 333 min |
| EMIM ethylsulfate | 29 ppm | PTZ | 20 ppm | 386 min |
| EMIM ethylsulfate/gamma-butyrolactone | 1000 ppm | PTZ | 20 ppm | 361 min |
| EMIM ethylsulfate/acetonitrile | 1000 ppm | PTZ | 20 ppm | 350 min |
| EMIM ethylsulfate/methyl butyl ketone | 44 ppm | PTZ | 20 ppm | 329 min |
| EMIM ethylsulfate/ethylenediamine | 25 ppm | PTZ | 20 ppm | 362 min |
| EMIM ethylsulfate/3-(dimethylamino)-1-propylamine | 29 ppm | PTZ | 20 ppm | 372 min |
| EMIM ethylsulfate/N-methylimidazole | 1000 ppm | PTZ | 20 ppm | 381 min |
| EMIM ethylsulfate/proglyme | 50 ppm | PTZ | 20 ppm | 352 min |
| TBA ether carboxylate | 22 ppm | PTZ | 20 ppm | 378 min |
| TBA ether carboxylate/methyl butyl ketone | 50 ppm | PTZ | 20 ppm | 336 min |
| TBA ether carboxylate/morpholine | 33 ppm | PTZ | 20 ppm | 344 min |
| TBA ether carboxylate/Agnique AMD 10 | 1000 ppm | PTZ | 20 ppm | 353 min |
| TBA ether carboxylate/ethylenediamine | 1000 ppm | PTZ | 20 ppm | 366 min |
| TBA ether carboxylate/3-(dimethylamino)-1-propylamine | 1000 ppm | PTZ | 20 ppm | 440 min |
| TBA ether carboxylate/N-methylimidazole | 1000 ppm | PTZ | 20 ppm | 416 min |
| TBA ether carboxylate/proglyme | 50 ppm | PTZ | 20 ppm | 338 min |

Pluriol A500 E = methyl polyethylene glycol;
Pluriol E 400 = polyethylene glycol;
Dowtherm A = eutectic mixture of biphenyl and diphenyl oxide;
Agnique AMD 3L = N,N-dimethyllactamide;
Agnique FOH 9 OC = oleyl/cetyl fatty alcohol;
Agnique FOH 898 = capryl alcohol;
Agnique AE 32 EH = 2-ethylhexyl lactate.

EXAMPLE 3

The solubility of phenothiazine in mixtures of 20% by weight of ionic liquid and 80% by weight of solvent was determined by gradually admixing the solutions with phenothiazine at room temperature until a significant phenothiazine precipitate could be observed. In the same way, the solubility of phenothiazine in the pure solvent was determined.

The following solvents were examined: dimethyl sulfate (DMSO), sulfolane, deionized water, benzonitrile, acetic acid, propionic acid, dimethyl succinate, methyl benzoate, γ-butyrolactone, acetonitrile, cyclohexanone, methyl butyl ketone, morpholine, ethylene glycol, methyl polyethylene glycol Mw 500 (Pluriol A 500 E), polyethylene glycol Mw 400 (Pluriol E 400), N,N-dimethyllactamide (Agnique AMD 3 L), dibutyl adipate (Cetiol B), di(2-ethylhexyl)adipate (Plastomoll DOA), n-octanol (Agnique FOH 898), C10 fatty acid dimethylamide (Agnique AMD 10), ethylenediamine, 3-(dimethylamino)-1-propylamine, N-methylimidazole, dimethylethyleneurea, 2-ethylhexyl lactate (Agnique AE 3-2 EH), benzyl alcohol, dimethyl phthalate, a eutectic mixture of biphenyl and diphenyl oxide (Dowtherm A), anisacetal, decahydronaphthalene, oleyl/cetyl fatty alcohol (Agnique FOH 9 OC), dipropylene glycol dimethyl ether (proglyme).

The relative solubilities of phenothiazine in a mixture of ionic liquid and solvent, based on the solubility of phenothiazine in the pure solvent, are shown in FIGS. 1 to 4. It can be seen that only a small solubility-increasing effect or solubility-reducing effect is observed in the case of protic solvents such as acetic acid, propionic acid, water, ethylene glycol, ethylenediamine.

EXAMPLE 4

Figure 5:
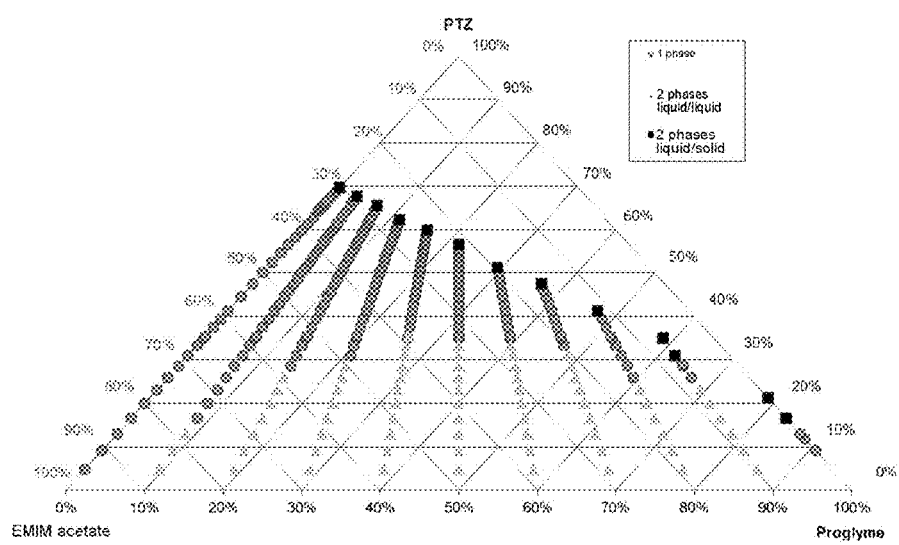
FIG. 5 shows the phase diagram (triangular diagram) of the system phenothiazine/proglyme/EMIM acetate.

The phase diagram (triangular diagram) of the system phenothiazine/proglyme/EMIM acetate was determined at room temperature. The phase diagram is shown in FIG. 5. In the triangular diagram, the corners correspond to the pure materials. The sides of the triangle correspond to two-component mixtures. The proportions of phenothiazine/proglyme/EMIM acetate at any point P are given by the intersections of the parallels to the side through P with the other sides. The phase behavior (single-phase, two phases liquid/liquid, two phases solid/liquid, three-phase) at selected points is indicated by symbols.

It can be seen that even small additions of the ionic liquid increase the solubility of phenothiazine in the solvent, with a linear increase up to the solubility in the pure ionic liquid being observed. It can also be seen that an incompatibility between the ionic liquid and the solvent (formation of two liquid phases) is eliminated by the addition of phenothiazine above a particular concentration.

EXAMPLE 5

Figure 6:
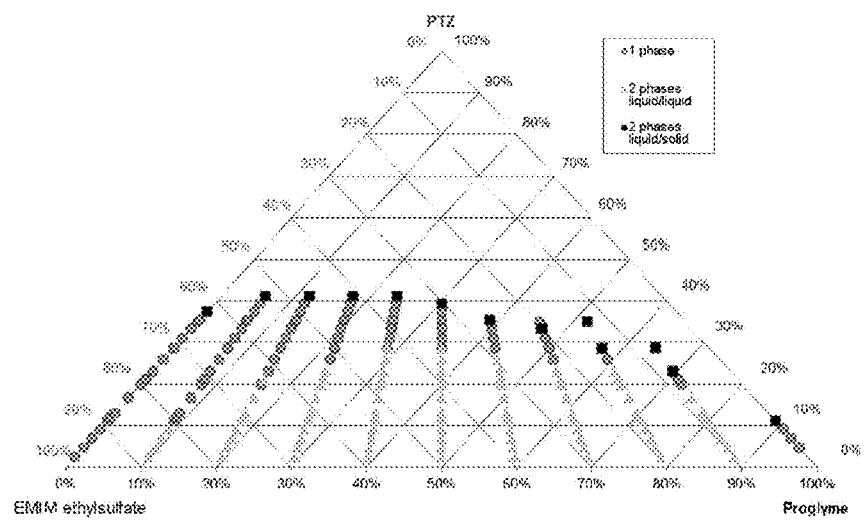
FIG. 6 shows the phase diagram (triangular diagram) of the system phenothiazine/proglyme/EMIM ethylsulfate.

The phase diagram (triangular diagram) of the system phenothiazine/proglyme/EMIM ethylsulfate was determined at room temperature. The phase diagram is shown in FIG. 6. In the triangular diagram, the corners correspond to the pure materials. The sides of the triangle correspond to two-component mixtures. The proportions of phenothiazine/proglyme/EMIM ethylsulfate at any point P are given by the intersections of the parallels to the sides through P with the other sides. The phase behavior (single-phase, two phases liquid/liquid, two phases solid/liquid, three-phase) at selected points is indicated by symbols.

It can be seen that even small additions of the ionic liquid increase the solubility of phenothiazine in the solvent, with a linear increase or a slight synergistic effect up to solubility in the pure ionic liquid being observed. It can also be seen that an incompatibility between the ionic liquid and the solvent (formation of two liquid phases) is eliminated by the addition of phenothiazine above a particular concentration.

The invention claimed is:

1. A composition, comprising
a) a phenothiazine free-radical polymerization inhibitor,
b) a polyol polyether aprotic solvent and
c) an ionic liquid.

2. The composition according to claim 1, wherein the composition comprises at least 20% by weight of the phenothiazine free-radical polymerization inhibitor, based on the total weight of components a), b) and c).

3. The composition according to claim 1, wherein the weight ratio of the polyol polyether aprotic solvent to the ionic liquid is in a range from 100:1 to 1:10.

4. The composition according to claim 1, wherein the polyol polyether aprotic solvent has a relative static permittivity $\varepsilon_r$ as liquid pure substance at a temperature of 293.15 K and a pressure of $1.0133 \cdot 10^5$ Pa in a range from 3 to 50.

5. The composition according to claim 1, wherein the polyol polyether aprotic solvent has a position in the Hansen solubility space which is such that $$\sqrt{4(\delta_D-17)^2+(\delta_P-11)^2+(\delta_H-6)^2} \leq 9$$

wherein:

$\delta_D$ denotes the LONDON dispersion forces, $\delta_P$ denotes the Debye interaction forces between permanent dipoles and also the Keesom interaction forces between induced and permanent dipoles and $\delta_H$ denotes the specific interaction forces.

6. The composition according to claim 1, wherein the ionic liquid comprises an organic cation selected from among quaternary ammonium, oxonium, sulfonium, phosphonium, uronium, thiouronium and guanidinium cations.

7. The composition according to claim 6, wherein the organic cation is selected from among quaternary ammonium ions, pyrrolium, imidazolium, 1H-pyrazolium, 3H-pyrazolium, 4H-pyrazolium, 1-pyrazolinium, 2-pyrazolinium, 3-pyrazolinium, 2,3-dihydroimidazolinium, 4,5-dihydroimidazolinium, 2,5-dihydroimidazolinium, pyrrolidinium, 1,2,4-triazolium (quaternary nitrogen atom in the 1 position), 1,2,4-triazolium (quaternary nitrogen atom in the 4 position), 1,2,3-triazolium (quaternary nitrogen atom in the 1 position), 1,2,3-triazolium (quaternary nitrogen atom in the 4 position), oxazolium, isoxazolium, thiazolium, isothiazolium, pyridinium, pyridazinium, pyrimidinium, piperidinium, morpholinium, pyrazinium, indolium, quinolinium, isoquinolinium, quinoxalinium and indolinium cations.

8. The composition according to claim 7, wherein the organic cation is selected from among quaternary ammonium ions of formula (II):

$$N^+R^1R^2R^3R^4 \qquad (II),$$

where $R^1$, $R^2$, $R^3$ and $R^4$ are, independently of one another, alkyl radicals which are optionally substituted by heterofunctional groups and optionally form aliphatic ring systems with one another, an imidazolium ion of formula (III)

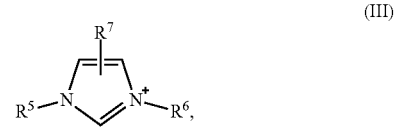

where $R^5$ is hydrogen or alkyl, $R^6$ is alkyl and $R^7$ is hydrogen or alkyl, an N-substituted pyridinium derivative, an N,N'-disubstituted pyrazolium derivative and an guadinium derivative.

9. The composition according to claim 8, wherein the organic cation is selected from among imidazolium cations.

10. The composition according to claim 1, wherein the ionic liquid comprises an anion selected from among carboxylates, sulfonates, phosphonates, halides, bis(trifluorosulfonyl)imides, aluminum tetrachloride, phosphorus fluoride and dicyanimides.

11. The composition according to claim 10, wherein the anion is selected from among alkylcarboxylates, polyether-comprising carboxylates and alkylsulfonates.

12. A method for stabilizing a free-radically polymerizable monomer, the method comprising:
stabilizing a free-radically polymerizable monomer against free-radical polymerization with the composition according to claim 1.

13. The method according to claim 12,
wherein the free-radically polymerizable monomers are selected from among 1-olefins, vinyl halides, vinylaromatics, vinyl ethers, vinyl esters, vinylamides, vinylcarboxylic acids, vinylaromatic carboxylic acids, acrylic acids, acrylic esters, acrylamides, acrylonitriles and allyl esters.

14. A method for immediately stopping free-radical polymerization, the method comprising:
adding the composition according to claim 1 to a free-radically polymerizing system.

15. The method according to claim 14, wherein
a commencement of an uncontrolled free-radical polymerization in the free-radically polymerizing system is registered when a temperature increase of the free-radically polymerizing system per unit time is above a prescribed value and
the composition is introduced into the free-radically polymerizing system.

* * * * *

UNITED STATES PATENT AND TRADEMARK OFFICE
CERTIFICATE OF CORRECTION

PATENT NO. : 10,221,255 B2
APPLICATION NO. : 15/735007
DATED : March 5, 2019
INVENTOR(S) : Ann-Kathrin Marguerre et al.

It is certified that error appears in the above-identified patent and that said Letters Patent is hereby corrected as shown below:

In the Specification

In Column 2, Line 43 (approx.), delete "dimethyibenzyl)" and insert -- dimethylbenzyl) --.

In Column 4, Line 29, delete "palmoleic" and insert -- palmitoleic --.

In Column 7, Line 26 (approx.), delete "CH$_2$O)CH$_2$" and insert -- CH$_2$O)$_n$CH$_2$ --.

In Column 8, Line 6, delete "(EMIM CI," and insert -- (EMIM Cl, --;
    Line 7, delete "(BMIM CI," and insert -- (BMIM Cl, --.

In Column 11, Lines 45-46, delete "$-PO_3^{2\ominus} M^{\oplus}$," and insert -- $-PO_3^{2\ominus} M2^{\oplus}$, --.

In the Claims

In Column 28, Line 31, Claim 8, delete "guadinium" and insert -- guanidinium --;
    Line 38, Claim 10, delete "dicyanimides" and insert -- dicyanamides --.

Signed and Sealed this
Twenty-sixth Day of May, 2020

Andrei Iancu
*Director of the United States Patent and Trademark Office*